US010821144B2

(12) United States Patent
Demais et al.

(10) Patent No.: US 10,821,144 B2
(45) Date of Patent: Nov. 3, 2020

(54) ALGAL EXTRACT COMPRISING SULPHATED AND NON-SULPHATED POLYANIONIC POLYSACCHARIDES AND USES THEREOF

(71) Applicant: Amadeite, Brehan (FR)

(72) Inventors: Hervé Demais, Merlevenez (FR); Sebastien Balusson, Saint Etienne du Gue de L'isle (FR)

(73) Assignee: AMADEITE, Brehan (FR)

( * ) Notice: Subject to any disclaimer, the term of this patent is extended or adjusted under 35 U.S.C. 154(b) by 0 days.

(21) Appl. No.: 16/017,862

(22) Filed: Jun. 25, 2018

(65) Prior Publication Data
US 2018/0303887 A1 Oct. 25, 2018

Related U.S. Application Data

(62) Division of application No. 14/651,345, filed as application No. PCT/EP2013/074105 on Nov. 18, 2013, now abandoned.

(30) Foreign Application Priority Data

Dec. 11, 2012 (FR) .................................... 12 61909

(51) Int. Cl.
A01N 65/00 (2009.01)
A61K 36/05 (2006.01)
A61K 31/737 (2006.01)

(52) U.S. Cl.
CPC ............ A61K 36/05 (2013.01); A61K 31/737 (2013.01)

(58) Field of Classification Search
USPC .................................................... 424/195.17
See application file for complete search history.

(56) References Cited

U.S. PATENT DOCUMENTS

2005/0196410 A1  9/2005  Daniels

FOREIGN PATENT DOCUMENTS

| JP | 2001342145 A | 12/2001 |
| JP | 2002212094 A | 7/2002 |
| JP | 2005245443 A | 9/2005 |
| WO | 2013/150253 A1 | 10/2013 |
| WO | 2014/090515 A1 | 6/2014 |

OTHER PUBLICATIONS

Lahaye M et al II: (Biomacromolecules, American Chemical Society, vol. 8 No. 6 pp. 1765-1774 Jun. 2007. (Year: 2007).*
Suganthy et al. ( Neuroscience Letters vol. 468, pp. 216-219 , 2010 (Year: 2010).*
Lahaye et al. I Journal of Applied Phycology, vol. 11, No. 1, Jan. 1999 (Year: 1999).*
Bin Hui et al. Journal of Neuroscience Research vol. 86, No. 5 pp. 1169-1177, Apr. 2008 (Year: 2008).*
Gennazzani et al. Effects of Klamath Algae extract on psychological disorders and depression in menopausal women: a pilot study 2010 (Year: 2010).*
Costa et al., "Characterization of Ulvan Extracts to Assess the Effect of Different Steps in the Extraction Procedure", Carbohydrate Polymers, 2012, pp. 537-546, vol. 88.
Hui et al., "Sulfated Polymannuroguluronate, a Novel Anti-Acquired Immune Deficiency Syndrome Drug Candidate, Decreased Vulnerability of PC12 Cells to Human Immunodeficiency Virus Tat Protein Through Attenuating Calcium Overload", Journal of Neuroscience Research, Apr. 1, 2008, pp. 1169-1177, vol. 86, No. 5.
Jaulneau et al., "An Ulva Armoricana Extract Protects Plants Against Three Powdery Mildew Pathogens", European Journal of Plant Pathology, 2011, pp. 393-401, vol. 131.
Kaeffer et al., "Biological Properties of Ulvan, a New Source of Green Seaweed Sulfated Polysaccharides, on Cultured Normal and Cancerous Colonic Epithelial Cells", Planta Medica, Aug. 1999, pp. 527-531, vol. 65.
Lahaye et al., "Chemical Composition and 13c NMR Spectroscopic Characterisation of Ulvans from Ulva (Ulvales, Chlorophyta)", Journal of Applied Phycology, Jan. 1, 1999, pp. 1-7, vol. 11, No. 1.
Lahaye et al., "Structure and Functional Properties of Ulvan, a Polysaccharide from Green Seaweeds", American Chemical Society—Biomacromolecules, Jun. 1, 2007, pp. 1765-1774, vol. 8, No. 6.
Office Action for JP Application 2015-546918 dated Aug. 29, 2017.
Patel, "Therapeutic Importance of Sulfated Polysaccharides from Seaweeds: Updating the Recent Findings", 3 Biotech, 2012, pp. 171-185, vol. 2.
Qi et al., "Antioxidant Activity of Different Molecular Weight Sulfated Polysaccharides from Ulva Pertusa Kjellm (Chlorophyta)", Journal of Applied Phycology, 2005, pp. 527-534, vol. 17.
Ray et al., "Cell-Wall Polysaccharides from the Marine Green Alga Ulva "rigida" (Ulvales, Chlorophyta). Extraction and Chemical Composition", Carbohydrate Research, 1995, pp. 251-261, vol. 274.
Robic et al., "Determination of the Chemical Composition of Ulvan, a Cell Wall Polysaccharide from Ulva spp. (Ulvales, Chlorophyta) by FT-IR and Chemometrics", Journal of Applied Phycology, 2009, pp. 451-456, vol. 21.
Robic et al., "Impact of Stabilization Treatments of the Green Seaweed Ulva rotundata (Chlorophyta) on the Extraction Yield, the Physico-Chemical and Rheological Properties of Ulvan", Carbohydrate Polymers, 2008, pp. 344-352, vol. 74.
Shao et al., "In Intro Antioxidant Activities of Different Sulfated Polysaccharides from Chlorophytan Seaweeds Ulva fasciata", International Journal of Biological Macromolecules, 2013, pp. 295-300, vol. 59.

(Continued)

Primary Examiner — Jana A Hines
Assistant Examiner — Khatol S Shahnan Shah
(74) Attorney, Agent, or Firm — Thompson Coburn LLP; Steven M. Ritchey

(57) ABSTRACT

The present invention relates to an algal extract comprising sulphated and non-sulphated polyanionic polysaccharides, to a method for preparing an algal extract as well as to its therapeutic and prophylactic applications.

14 Claims, 8 Drawing Sheets

(56) References Cited

OTHER PUBLICATIONS

Figure 1:
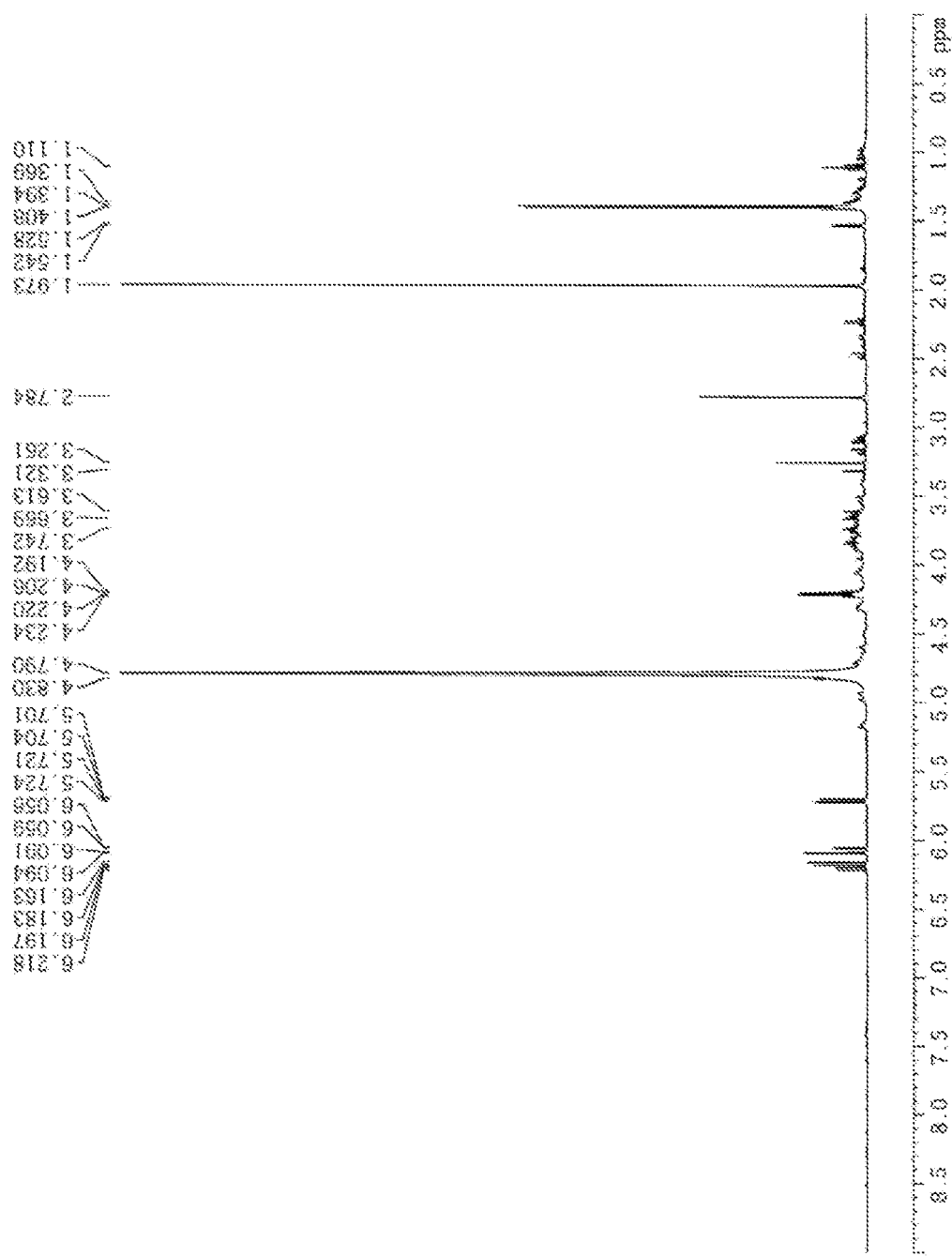

Suganthy et al., "Neuroprotective Effect of Seaweeds Inhabiting South Indian Coastal Area (Hare Island, Gulf of Mannar Marine Biosphere Reserve): Cholinesterase Inhibitory Effect of Hypnea Valentiae and Ulva Reticulata", Neuroscience Letters, 2010, pp. 216-219, vol. 468.

Yamamoto et al., "Physicochemical Characterization of Sulfated Polysaccharides from Green Seaweeds: *Ulva pertusa* and *Ulva conglobata*", Agricultural and Biological Chemistry, 1980, pp. 723-729, vol. 44, No. 4.

Yamamoto, "Physicochemical Studies on Sulfated Polysaccharides Extracted from Seaweeds at Various Temperatures", Agricultural and Biological Chemistry, 1980, pp. 589-593, vol. 44, No. 3.

Allaert et al., "A randomized controlled double-blind clinical trial comparing versus placebo the effect of an edible algal extract (*Ulva lactuca*) on the component of depression in healthy volunteers with anhedonia," BMC Psychiatry (2018) 18:215, 10 pages.

Porsolt et al., "Behavioural despair in rats: a new model sensitive to antidepressant treatments," European Journal of Pharmacology, 47(1978) pp. 379-391.

Violle et al., "Evaluation of the Antidepressant- and Anxiolytic-Like Effects of a Hydrophilic Extract from the Green Seaweed *Ulva* sp. in Rats", Nutritional Neuroscience, 2017, pp. 1-9.

\* cited by examiner

# P < 0.10 (Trend)    (Wicoxon's test: LA vs. LI).

# P < 0.10 (Trend) ; * P < 0.05 (Wicoxon's test: LA vs. LI).

* P < 0.05 (Wicoxon's test: LA vs. LI).

ALGAL EXTRACT COMPRISING SULPHATED AND NON-SULPHATED POLYANIONIC POLYSACCHARIDES AND USES THEREOF

CROSS-REFERENCE TO RELATED APPLICATIONS

This is a divisional application of U.S. Ser. No. 14/651,345, filed on Jun. 11, 2015, which was a national stage application of PCT/EP2013/074105, filed on Nov. 18, 2013, which claims the benefit of FR 12 61909, filed on Dec. 11, 2012, each of which is incorporated herein by reference in its entirety.

FIELD OF THE INVENTION

The present invention relates to an algal extract comprising sulphated and non-sulphated polyanionic polysaccharides, and to a method for preparing an algal extract, as well as to its therapeutic and prophylactic applications.

BACKGROUND OF THE INVENTION

The *Ulva* species (Ulvales, Chlorophyta) are abundant algae found in the intertidal or foreshore area. They colonize hard substrates, anchored by an attachment disc, but certain species may also give rise to free drifting living forms. *Ulva* algae are fast growing algae and opportunistic as to space and absorption of nutrients. Their growth in the water column is particularly observed in eutrophised coastal waters and in lagoons where *Ulva* sp. proliferates in the form of "green tides" (Fletcher, 1996). Often mass production and mass strandings, producing noxious gases when they accumulate, result from this (Morand and Briand, 1996). Up till now, this biomass had very little added value and the means for using it except for compost (Mazé et al. 1993, Cuomo et al. 1995), for producing methane (Briand and Morand, 1997), for human food consumption (Pérez, 1997) or as a basis for paper (Nicolucci and Monegato 1993) might give the possibility of making the most out of their specific properties.

At the present time, the use of green algae is essentially based on uses giving the possibility of opening new routes for removing these algae considered as undesirable. The contemplated application routes concern the production of biogas (Briand & Morand 1997, Morand & Briand 1999, Morand et al., 2006), biomaterials (bioplastics) (Chiellini et al., 2008), biodegradable cups (Sassi et al., 2008), papers and cardboards for packaging (Nicolucci & Monegata et al., 1993), charge nano-composites (Demais et al., 2006a, 2006b), animal nutrition: detoxifying feed for animals (Demais et al., 2006), proteins and appetence factors for fish farming (DeBose et al., 2008, Kut Guroy et al., 2007) and cosmetics (surfactants) (Ranson et al., 2008).

The chemical and physico-chemical properties of the polysaccharides contained in these algae make them attractive candidates as novel functional and biologically active polymers in the fields of human and animal consumption, of pharmaceutics, of chemistry, of fish farming and agriculture (Robic A, et al. Carbohydrate Polymers 77 (2009) 206-216; Lahaye M Robic A, Biomacromolecules Vol 8 No. 6, 2007).

DETAILED DESCRIPTION OF THE INVENTION

According to one of these aspects, the present invention relates to an extract from algae of the order of the Ulvales, in particular an extract from green algae of the *Ulva* type, comprising sulphated and non-sulphated polyanionic polysaccharides, the size of which is less than or equal to 50 kDa.

In particular, said polysaccharides of the algal extract according to present invention comprise mannose and/or arabinose. More particularly, said polysaccharides comprise at least 0.005% of mannose and/or at least 0.005% of arabinose, by weight based on the weight of the total dry material of the algal extract, notably at least 0.01% of mannose and/or at least 0.01% of arabinose. Still more particularly, said polysaccharides comprise mannose in an amount ranging from 0.01 to 0.20% and arabinose in an amount ranging from 0.01 to 0.5%, by weight based on the weight of the total dry material of the algal extract, notably mannose in an amount ranging from 0.03 to 0.15% and arabinose in an amount ranging from 0.01 to 0.2%.

In particular, said polysaccharides further comprise:
  galactose;
  glucose;
  rhamnose;
  xylose; and
  glucuronic acid.

Sill more particularly, said polysaccharides comprise:
  from 0.05 to 0.5% of galactose, notably from 0.1 to 0.4%;
  from 0.005 to 0.05% of glucose, notably from 0.01 to 0.03%;
  from 2 to 15% of rhamnose, notably from 5 to 10%;
  from 0.1 to 1% of xylose, notably from 0.3 to 0.7%; and
  from 1 to 7% of glucuronic acid, notably from 1 to 5%;
by weight based on the weight of the total dry material of the algal extract.

Thus, mention may for example be made of an algal extract according to the invention comprising:
  mannose;
  arabinose;
  galactose;
  glucose;
  rhamnose;
  xylose; and
  glucuronic acid.

More particularly mention may for example be made of an algal extract according to the invention comprising:
  from 0.01 to 0.20% of mannose, notably from 0.03 to 0.15%;
  from 0.01 to 0.5% of arabinose, notably from 0.01 to 0.2%;
  from 0.05 to 0.5% of galactose, notably from 0.1 to 0.4%;
  from 0.005 to 0.05% of glucose, notably from 0.01 to 0.03%;
  from 2 to 15% of rhamnose, notably from 5 to 10%;
  from 0.1 to 1% of xylose, notably from 0.3 to 0.7%; and
  from 1 to 7% of glucuronic acid, notably from 1 to 5%;
by weight based on the weight of the total dry material of the algal extract.

Still more particularly mention may for example be made of an algal extract according to the invention comprising:
  0.09% of mannose;
  0.1% of arabinose;
  0.3% of galactose;
  0.02% of glucose;
  8.1% of rhamnose;
  0.5% of xylose; and
  2.6% of glucuronic acid;
by weight based on the weight of the total dry material of the algal extract.

More particularly, the algal extract according to the present invention comprises sulphated and non-sulphated polyanionic polysaccharides for which the size is less than 40, 30, 20 or 15 kDa. Still more particularly, the sulphated and non-sulphated polyanionic polysaccharides of the algal extract according to the invention has a size of less than or equal to 15 kDa.

A dalton (Da) is a mass unit defined as being equal to one-twelfth of the mass of a carbon 12 atom, a mass which will subsequently be estimated from a mixture of several isotopes (mainly carbon 12 and carbon 13, respectively having 6 and 7 neutrons in addition to the 6 protons like any carbon atom). One dalton is, with quite good accuracy, the mass of a hydrogen atom, the exact value being 1.00794 amu (atomic mass unit). The kilodalton (kDa) is equal to 1,000 Da.

Within the scope of the present invention, the masses mentioned in kDa are determined by any method usually used by one skilled in the art, in particular the masses of the sulphated and non-sulphated polyanionic polysaccharides of the algal extracts according to the present invention may be discriminated by ultrafiltration on membranes only letting through molecules of predetermined sizes.

By "green algae of the *Ulva* type" are meant the green algae grouped in the genus *Ulva* from the family of Ulvaceae, of the order of the ulvales. Mention may notably be made of the following species and sub-species: *Ulva acanthophora, Ulva anandii, Ulva angusta, Ulva arasakii, Ulva armoricana, Ulva atroviridis, Ulva attenuata, Ulva beytensis, Ulva bifrons, Ulva brevistipitata, Ulva bulbosa, Ulva burmanica, Ulva byssoides, Ulva californica, Ulva chaetomorphoides, Ulva clathrata, Ulva coccinea, Ulva compressa, Ulva conglobata, Ulva cornucopiae, Ulva cornuta, Ulva covelongensis, Ulva crassa, Ulva crassimembrana, Ulva curvata, Ulva dactylifera, Ulva denticulata, Ulva elegans, Ulva elminthoides, Ulva enteromorpha, Ulva erecta, Ulva expansa, Ulva fasciata, Ulva fenestrata, Ulva flexuosa, Ulva gelatinosa, Ulva geminoidea, Ulva gigantea, Ulva grandis, Ulva hendayensis, Ulva hookeriana, Ulva hopkirkii, Ulva indica, Ulva intestinalis, Ulva intestinaloides, Ulva intricata, Ulva intybacea, Ulva javanica, Ulva kylinii, Ulva lactuca, Ulva lactucaefolia, Ulva laetevirens, Ulva laingii, Ulva linearis, Ulva lingulata, Ulva linkiana, Ulva linza, Ulva lippii, Ulva litoralis, Ulva littorea, Ulva lobata, Ulva lubrica, Ulva marginata, Ulva micrococca, Ulva myriotrema, Ulva neapolitana, Ulva nematoidea, Ulva ohnoi, Ulva olivacea, Ulva olivaceum, Ulva pacifica, Ulva papenfussii, Ulva paradoxa, Ulva parva, Ulva parvula, Ulva patengensis, Ulva percursa, Ulva pertusa, Ulva phyllosa, Ulva popenguinensis, Ulva porrifolia, Ulva procera, Ulva profunda, Ulva prolifera, Ulva pseudocurvata, Ulva pseudolinza, Ulva pulchra, Ulva purpurascens, Ulva quilonensis, Ulva radiata, Ulva ralfsfi, Ulva ranunculata, Ulva reticulata, Ulva rhacodes, Ulva rigida, Ulva rotundata, Ulva rubens, Ulva saifullahfi, Ulva scagelii, Ulva scandinavica, Ulva sericea, Ulva serrata, Ulva simplex, Ulva sorensenii, Ulva spinulosa, Ulva stenophylla, Ulva stipitata, Ulva sublittoralis, Ulva subulata, Ulva taeniata, Ulva tenera, Ulva tetragona, Ulva torta, Ulva tuberosa, Ulva umbilicata, Ulva uncialis, Ulva uncinata, Ulva usneoides, Ulva utricularis, Ulva utriculosa, Ulva uvoides, Ulva ventricosa.*

More particularly, the algal extract according to the invention is an extract from algae of the *Ulva armoricana* species.

According to an embodiment of the invention, the algal extract comprises:
from 10 to 50% of carbon;
from 1 to 10% of hydrogen;
from 1 to 5% of nitrogen;
from 20 to 50% of oxygen; and
from 1 to 15% of sulphur;
in percent by mass of the total dry material of the algal extract.

Still more particularly, the algal extract comprises:
from 15 to 30% of carbon;
from 3 to 6% of hydrogen;
from 1 to 3% of nitrogen;
from 25 to 40% of oxygen; and
from 2.5 to 10% of sulphur;
in mass percentage of the total dry material of the algal extract.

The other chemical elements present in the dry material of the extract are notably represented by the minerals (Ca, K, Na, Mg, Al, Cl, I, P, Fe, etc).

More particularly, the algal extract according to the invention is characterized by the $^1$H NMR spectrum shown in FIG. 1.

This $^1$H NMR spectrum was recorded at 298 K on a Bruker Avance 500 spectrometer equipped with an inverse TCI cryogenic probe 5 mm $^1$H/$^{13}$C/$^{15}$N. Before the analysis, the samples were dissolved in 99.97% of D$_2$O atoms. The chemical shifts are expressed in ppm relatively to an external standard (trimethylsilylpropionic acid). No suppression of the HOD signal was achieved.

According to another of these aspects, the present invention relates to a method for producing an extract from algae of the order of ulvales, in particular an extract from green algae of the *Ulva* type, wherein:
 a) the algae are washed and freed of sand;
 b) said algae are crushed;
 c) the solid phase of the crushed product is separated from its liquid phase;
 d) said liquid phase is clarified;
 e) the juice obtained in step d) is ultrafiltrated; and
 f) the filtration juice obtained in step e) is concentrated and then dried.

According to an embodiment of the method according to the present invention, the algae are washed with fresh water.

Sand may be removed from them by any means made available to one skilled in the art.

Said algae are then milled, notably by means of a milling machine, such as for example a refiner or a cutter.

Subsequently, the solid phase of the milled product, the marc, is separated from its liquid phase, the juice, by pressing the milled product, for example by means of a belt or plate press or by centrifugation.

By "juice", is meant the cytoplasm juice which includes the wall structure of the double structure of the cells of the algae.

The obtained liquid phase is then clarified, for example with a clarifier with disk stacks, or by centrifugation, decantation or filtration (for example with a pocket or a plate).

The obtained juice is then ultrafiltrated.

According to an embodiment of the method according to the present invention, ultrafiltration is carried out on a membrane of less than 50 kDa, notably on a 40, 30, 20 or 15 kDa membrane. More particularly, the membrane will be a 15 kDa membrane.

This membrane may for example be a ceramic membrane or an organic membrane. More particularly, the membrane will be a ceramic membrane.

The obtained filtration juice may then be concentrated, for example by reverse osmosis, evaporation or precipitation, and then for example dried by freeze-drying or atomization.

Optionally, the obtained extract may then again be crushed, in order to obtain a homogeneous powder in terms of grain size.

According to one of these aspects, the method according to the invention partly takes place at room temperature. By room temperature is meant a temperature comprised between 5 and 25° C.

According to another of these aspects, the method according to the invention partly takes place at a temperature comprised between 4 and 10° C., this in order to avoid microbial growth.

This method differs from most methods described in the prior art because of the absence of a step involving precipitation of the algal extract. It is also distinguished from the previous extraction methods by the absence of any use of solvents, in particular organic solvents, which represents a major advantage from an ecological point of view.

According to another of these aspects, the present invention relates to an algal extract which may be obtained by the method as described earlier.

According to another of these aspects, the present invention relates to an algal extract as defined above which may be obtained by the method as described earlier.

According to one of these aspects, the present invention also relates to a pharmaceutical composition comprising an algal extract as described earlier as well as to a pharmaceutically acceptable excipient.

According to one of these aspects, the present invention also relates to an algal extract as described earlier for its use as a drug.

According to one of these aspects, the present invention also relates to an algal extract as described earlier for its use in preventing and/or treating neurological disorders, depression, stress, anxiety, as an agent allowing improvement of memory notably in preventing and/or treating ageing or Alzheimer's disease, in preventing and/or treating neuropathic and inflammatory chronic pain, skin pain (of the skin, of subcutaneous tissues and associated organs) or body pain.

According to another of these aspects, the present invention also relates to the use of an algal extract as described earlier as a drug.

According to one of these aspects, the present invention also relates to the use of an algal extract as described earlier in preventing and/or treating neurological disorders, depression, stress, anxiety, as an agent allowing improvement of memory notably in preventing and/or treating ageing or Alzheimer's disease, in preventing and/or treating neuropathic and inflammatory chronic pain, cutaneous pain (of the skin, subcutaneous tissues and associated organs) or body pain.

By "neurological disorders" are meant diseases of the nervous system, in particular of the brain. Among these diseases, mention may notably be made of brain pathologies such as Parkinson's disease, multiple sclerosis, Alzheimer's disease, dementia, migraines, headaches.

By "depression" is meant a mood disorder essentially characterized by a condition with loss of motivation or vital momentum in an individual, either associated or not with different symptoms. The most characteristic symptoms are a loss of hope, of desire, of self-esteem. Other signs may occur, such as fatigue, sadness, negative thoughts, dark thoughts, suicidal intentions, anxiety or fear or in certain extremely rare cases, hallucinations.

This term of depression is again found under the names of "recurrent depressive disorder", "nervous breakdown", "clinical depression", "unipolar depression", "major depressive and characterized episode" or further "depressive syndrome". The term of "depressions" designates the whole of the types of depression. The terms of "depressivity" or "depressive feeling" are also used. Common language also mentions "feeling low", which has similar symptoms, but more attenuated.

By "stress", is meant the whole of the responses of an organism subject to pressures or constraints from its environment. These responses always depend on the perception which the individual has of the pressures which he/she feels. This is a complex sequence of events causing physiological and psychosomatic responses.

By "anxiety", is meant a psychological and physiological condition characterized by somatic, emotional, cognitive and behavioural components. In the absence or in the presence of psychological stress, anxiety may generate feelings of fear, restlessness, difficulty and worries. Anxiety is considered as a normal reaction in a stressing situation. When anxiety becomes excessive, it may be classified under the name of "anxiety disorder".

Thus, an algal extract according to the present invention may be used both in veterinary applications, such as for example for preventing and/or treating stress in livestock and pets or as an anti-depressant agent for livestock or pets, and in applications intended for humans, for example via food supplements with a health purpose without any secondary effects or a drug, in order for example to prevent and/or treat disorders related to stress, to anxiety, to depression, as well as an agent allowing improvement in memory, notably in students, for combating ageing or further within the scope of treating Alzheimer's disease.

The pharmaceutically acceptable excipients are selected according to the pharmaceutical form and to the desired administration route, from among usual excipients which are known to one skilled in the art.

In the pharmaceutical compositions of the present invention for oral, sublingual, subcutaneous, intramuscular, intravenous, topical, local, intratracheal, intranasal, transdermal or rectal administration, the algal extract as defined above may be administered as unit doses, mixed with conventional pharmaceutical excipients to animals and to human beings, for preventing or treating the aforementioned disorders.

The suitable administration forms comprise oral forms such as tablets, soft or hard gelatin capsules, powders, granules or oral solutions or suspensions, sublingual, buccal, intratracheal, intraocular, intranasal administration forms, by inhalation, topical, parenteral such as transdermal, subcutaneous, intramuscular or intravenous administration forms, rectal administration forms and implants. For topical application, the compounds according to the invention may be used in creams, gels, ointments or lotions.

When a solid composition such as tablets is prepared, the main active ingredient may be mixed with a pharmaceutical carrier such as gelatin, starch, lactose, magnesium stearate, talcum, gum arabic or the like.

The tablets may also be coated with saccharose, a cellulose derivative, or other suitable materials or further they may be treated so that they have a prolonged or delayed activity and continuously release a predetermined amount of active ingredient.

A preparation as gelatin capsules may for example be obtained by mixing the active ingredients with a diluent and by pouring the obtained mixture into soft or hard gelatin capsules.

The pharmaceutical compositions containing an algal extract according to the invention, may also appear in liquid from, for example, as solutions, emulsions, suspensions or syrups, and notably in a suitable form for oral or intranasal administration for example. The suitable liquid supports may for example be water, organic solvents such as glycerol or glycols, as well as their mixtures, in varied proportions, in water.

A preparation as a syrup or elixir or for administration in drop form may also contain the active ingredient together with an acaloric sweetener for example, methylparabene or propylparabene as an antiseptic, as well as an agent providing taste and a suitable colouring agent.

The powders or the granules dispersible in water may for example contain the active ingredient mixed with dispersion agents or wetting agents, or suspension agents, such as polyvinylpyrrolidone, also with sweeteners or flavour correctors.

The dose administered daily in humans may attain 0.5 to 25 mg/kg, in one or several takings, in particular from 1.5 to 18 mg/kg, and still more particularly from 3 to 15 mg/kg. The daily administered dose in animals may attain 5 to 150 mg/kg, in one or several takings, in particular from 10 to 100 mg/kg and even more particularly from 20 to 80 mg/kg. Generally, the daily dose of the algal extract according to the invention will be the smallest effective dose of the algal extract capable of producing a therapeutic effect.

By "effective dose", is meant any amount of a composition which improves one or several of the characteristic parameters of the disease or of the disorder to be treated.

There may be particular cases where higher or lower dosages are suitable; such dosages do not depart from the scope of the present invention. According to customary practice, the suitable dosage for each patient, human or animal is determined by the physician or the veterinary surgeon according to the administration route, the weight and the response of said patient.

According to another of its aspects, an algal extract according to the present invention may be used for preventing and/or treating the aforementioned pathologies in a food composition.

By "food composition" is for example meant any type of nutraceutical, of food products as a yogurt or a drink, notably a dairy drink, any type of raw material, technological additive or auxiliary, in the form of pre-mixes, either medicinal or not, intended to be incorporated into foodstuffs, any type of full or supplement foodstuffs, intended for humans or animals.

The present invention, according to another of its aspects, also relates to a method for treating the pathologies indicated above which comprises administration to a patient of an effective dose of an algal extract according to the invention.

The present invention will be illustrated in more detail by the figures and examples below which do not limit the scope thereof.

FIGURES

FIG. 1: $^1$H NMR spectrum of an algal extract (AE) according to the present invention.

Figure 2:
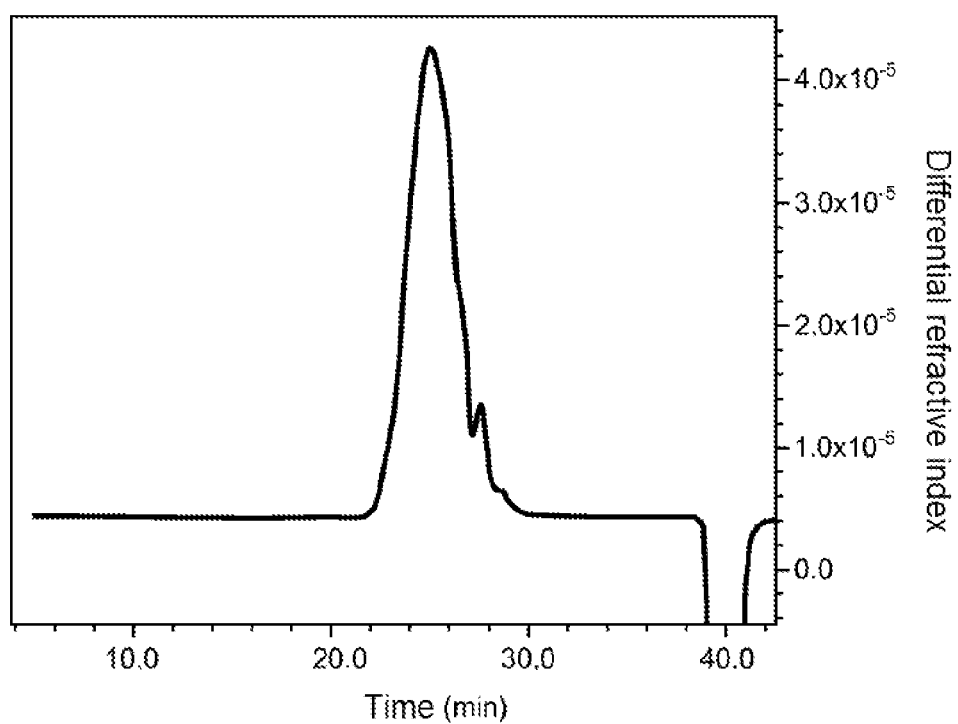

FIG. 2: Chromatogram obtained with the algal extract according to the invention separated on two Shodex 802 and 803 columns.

Figure 3:
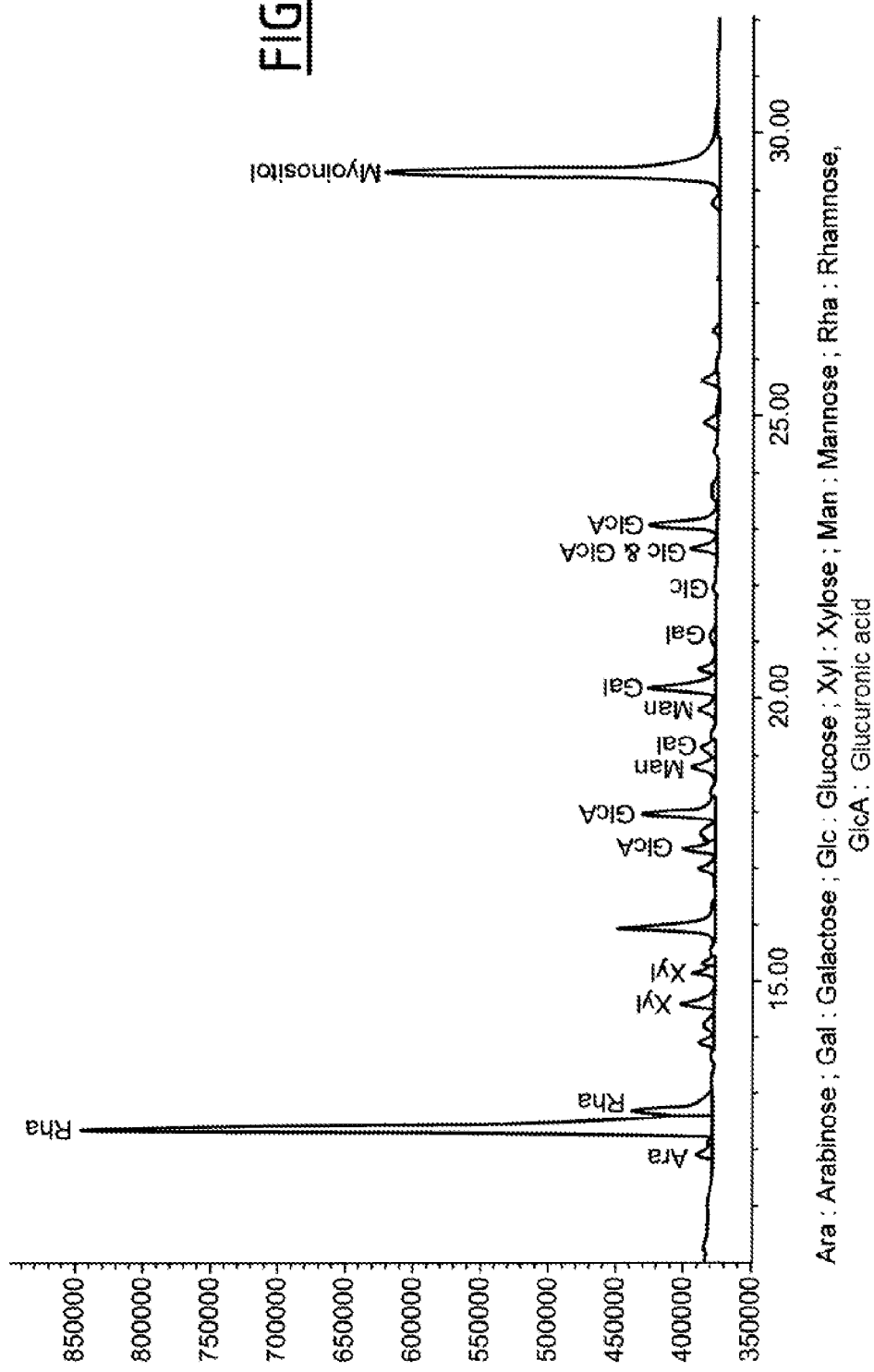

FIG. 3: Chromatogram obtained after analysis of trimethylsilylated derivatives of the sample of the algal extract according to the invention by gas chromatography. With Ara: Arabinose; Gal: Galactose; Glc: Glucose; Xyl: Xylose; Man: Mannose; Rha: Rhamnose; GlcA: Glucuronic acid.

Figure 4:
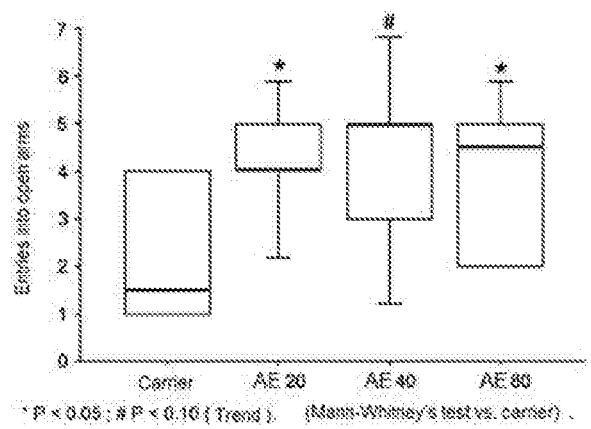

FIG. 4: Effects of AE on the number of entries into the open arms in the elevated plus-maze test.

Figure 5:
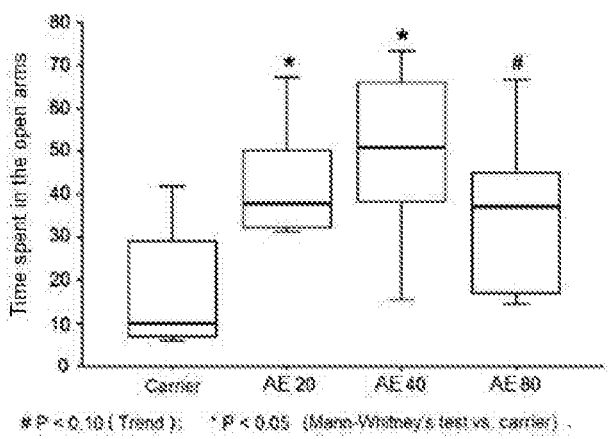

FIG. 5: Effects of AE on the time spent in the open arms in the elevated plus-maze test.

Figure 6:
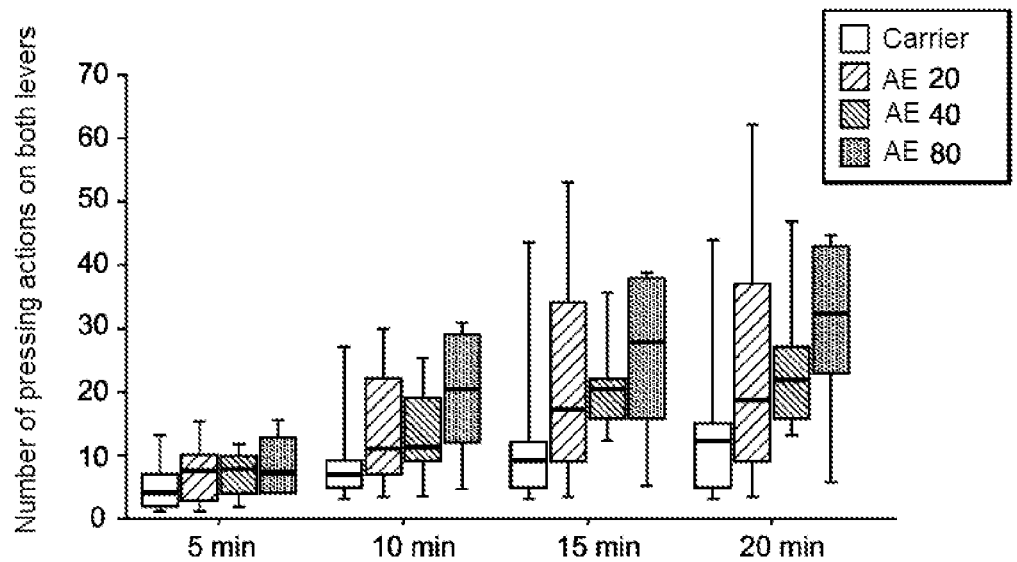

FIG. 6: Effects of AE on the total number of cumulated pressing actions on both levers in the learning test for avoiding an aversive light stimulus (ALSAR for Aversive Light Stimulus Avoidance Response).

Figure 7:
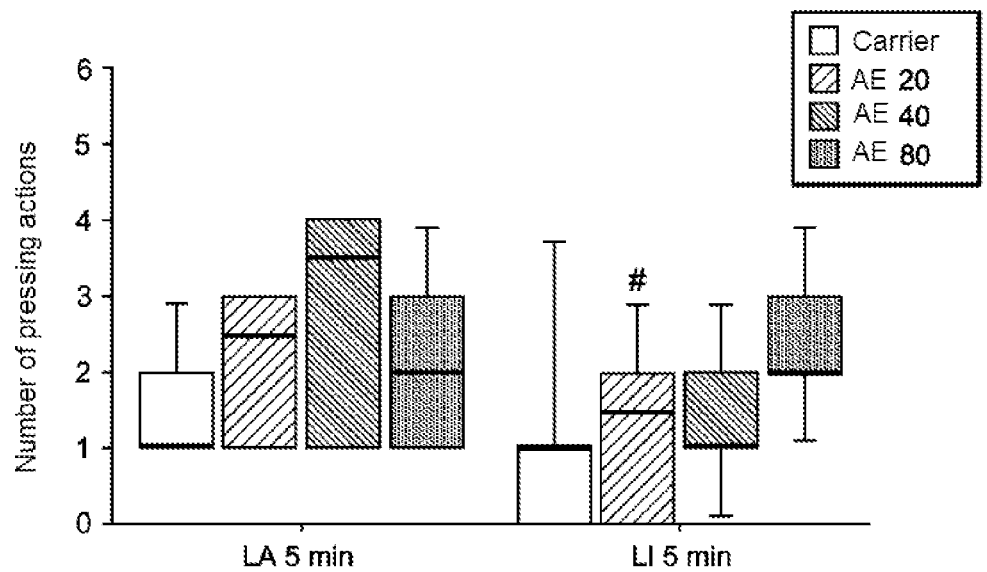

FIG. 7: Effects of AE on the total number of pressing actions on the active levers (LA) and inactive levers (LI) at 5 minutes in the ALSAR test.

Figure 8:
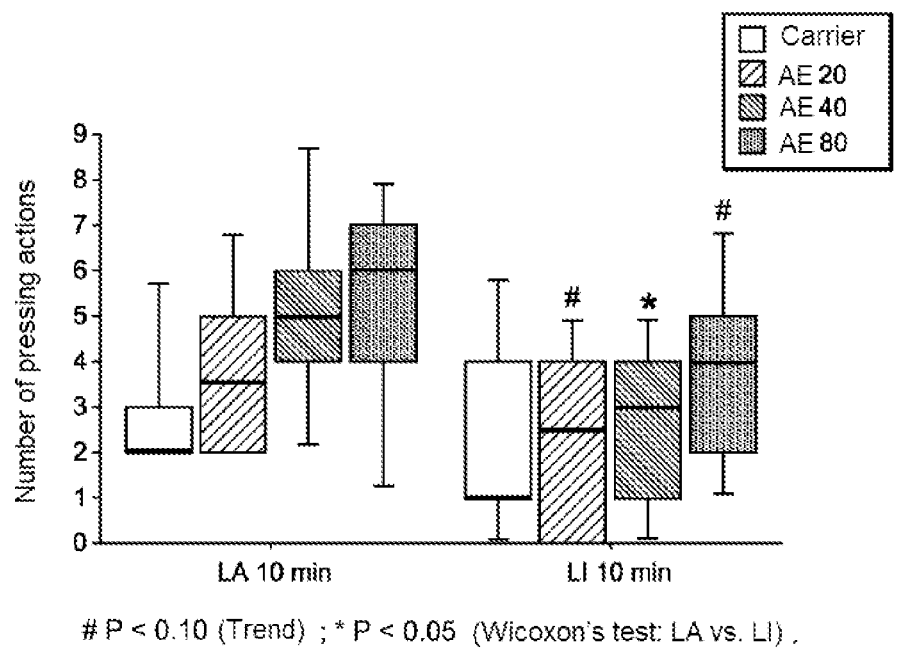

FIG. 8: Effects of AE on the total number of pressing actions on the active levers (LA) and inactive levers (LI) at 10 minutes in the ALSAR test.

Figure 9:
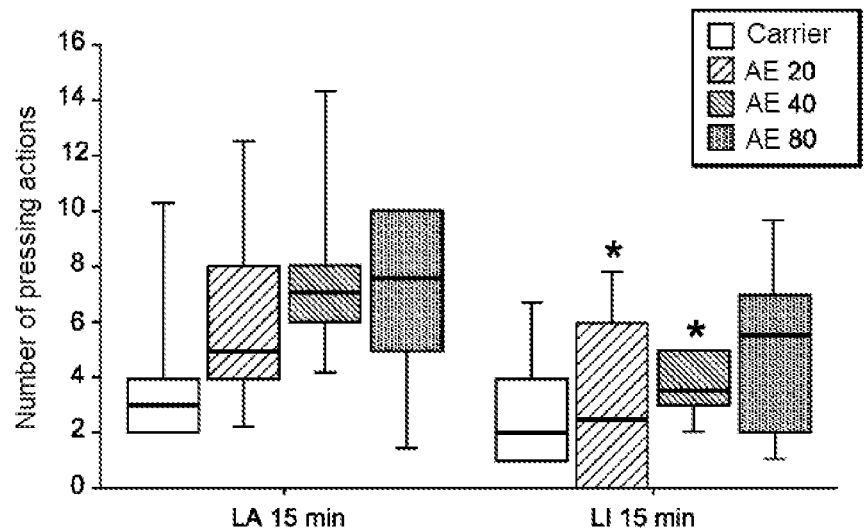

FIG. 9: Effects of AE on the total number of pressing actions on the active levers (LA) and inactive levers (LI) at 15 minutes in the ALSAR test.

Figure 10:
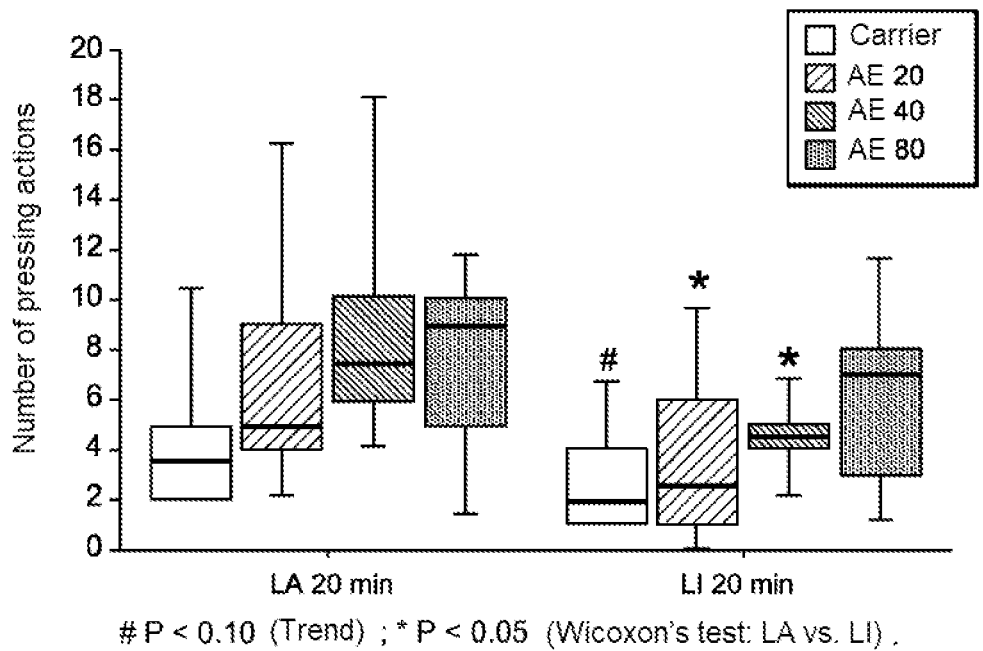

FIG. 10: Effects of AE on the total number of pressing actions on the active levers (LA) and inactive levers (LI) at 20 minutes in the ALSAR test.

Figure 11:
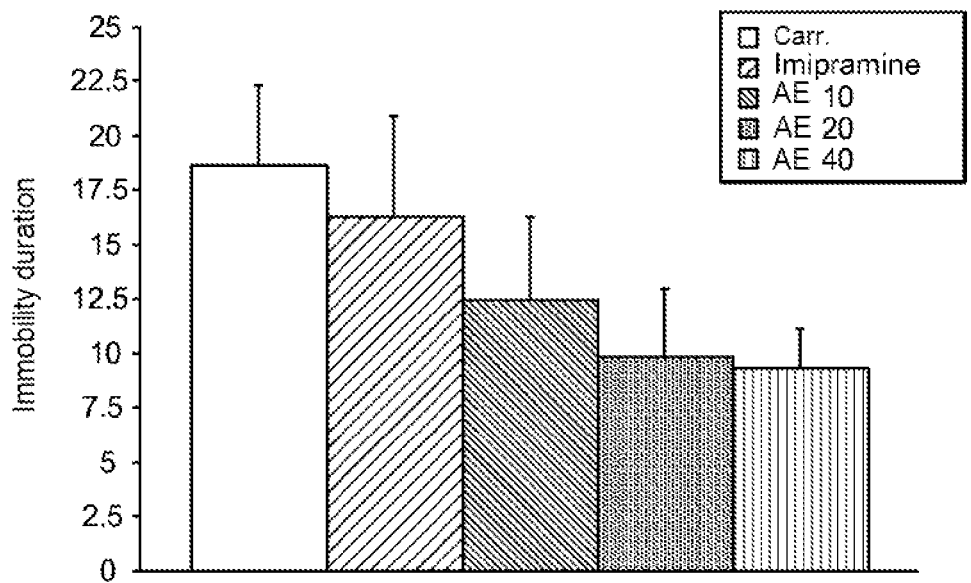

FIG. 11: Effects of AE on the duration of immobility(ies) in the pre-test of behavioural despair at D14 (s, Average±SME).

Figure 12:
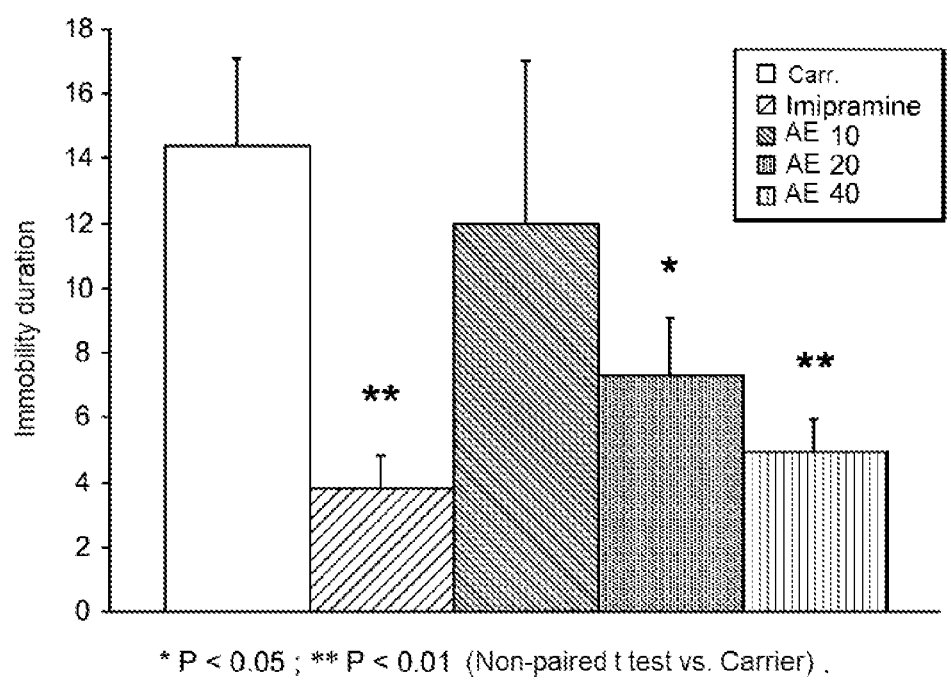

FIG. 12: Effects of AE on the duration of immobility(ies) in the behavioural despair test at D15 (s, Average±SME).

EXAMPLES

Example 1: Preparation of an Algal Extract According to the Invention

One metric ton of fresh, raw, green algae of the *Ulva* type, is washed with fresh water and sand is removed by means of a machine for washing algae.

Unless indicated otherwise, the steps of the method are carried out at room temperature.

The algae (1 metric ton of drained algae with 8% dry material) are then crushed into fine particles by means of an industrial refiner (Inotec brand type "I175CDI-75D"). By "fine particles" are meant particles for which the size is comprised between 50 and 1,000 nm, with two populations, the first for which the sizes are comprised between 50 and 200 nm, the second for which the sizes are comprised between 600 and 1,000 nm.

The crushed material was then pressed by means of an industrial belt press of the brand Flottweg type "B FRU 800 HK", at a throughput of about 1 metric ton/hour.

This step allows separation of the solid phase (marc) from the liquid phase (juice). The yield of obtained juice is 75%.

The 750 kg of raw juice obtained are then clarified by means of a clarifier with disc stacks of the brand Flottweg type "AC 2000".

710 kg of a clear juice with 3.10% of dry mass (95 to 98% mass yield) and a cream (2 to 5% by mass) are thereby obtained.

Subsequently, the clear juice is ultrafiltrated on a ceramic membrane (Tami Industries) of 15 kDa.

A permeate and a retentate are thereby obtained. The permeate is kept until 640 kg of filtration juice (91% of volume yield) with 2.2% of dry material are obtained.

The filtration juice (permeate) is then dried by freeze-drying after concentration by evaporation.

The concentration is achieved on a simple effect evaporator (EVA 1000, Pignat) with the following parameters: forced reflow, supply flow rate 10 L/h, vapour pressure of 1 bar, vacuum pressure of 0.3 bars and evaporation temperature of 90° C.

A first concentration is achieved with an evaporated water flow of 8 L/h and the Brix degree rises from 5.5 (equal to a dry material concentration of 4.5%) to 14.7. This solution is then concentrated a second time with an evaporated water flow of 5-6 L/h and the Brix degree rises up to 34. The dry material concentration of the solution is determined at 38.4%.

Freeze-drying is then carried out by means of a Bioblock scientific apparatus (version CHRIST alpha 1-4 LSC) at a freezing temperature of −80° C. which is also the minimum temperature during this step.

The obtained powder is then crushed with a planetary milling machine MiniMill of the Philips brand. The product was introduced into milling bowls (10 g of product in each milling bowl with 4 zirconia balls). The whole was set into rotation for 15 minutes at speed 10.

14 kg of an algal extract powder were thereby obtained.

Example 2: Determination of the Size of Sulphated and Non-Sulphated Polyanionic Polysaccharides of an Algal Extract According to the Invention by GPC (Gel Permeation Chromatography)

The algal extract according to the invention and prepared according to Example 1 is ultrafiltrated on a 1,000 Da membrane and is dissolved at a concentration of 0.5 g/L in water. It is then injected on two Shodex 802 and 803 columns placed in series (fractionation domain of the 802 column: $4.10^3$ Da and of the 803 column: $1.7.10^5$ Da). The eluent used is 0.1 M sodium nitrate with 0.2% sodium azide at a flow rate of 0.5 ml/min. Detection is achieved via a Wyatt refractometre and an 18-angle light scattering detector Wyatt. The do/dc are assumed to be equal to 0.150 ml/g.

The chromatogram detected by the refractometre is shown in FIG. 2.

An average size of 4.4 kDa of the polysaccharides from an algal extract according to the invention is obtained.

Example 3: Determination of the Composition of an Algal Extract According to the Invention The algal extract according to the invention and prepared according to Example 1 is purified by front ultrafiltration in amicon cells operating with stirring. A regenerated cellulose membrane with a cut-off threshold of 1,000 Da is used. 572.1 mg of a sample of algal extract according to the invention are dissolved in 150 ml of ultrapure milli-Q water. Five litres of water are used for removing all the molecules with a mass of less than 1,000 Da. The retentate is freeze-dried. 117 mg of sample are weighed. The ultrafiltration yield is therefore 20.5% (w/w). The following analyses were carried out on ultrafiltrated samples.

The ratio of the monosaccharides making up the polysaccharides of the algal extract according to the invention is determined according to the Kamerling method (Kamerling et al., 1975) modified by Montreuil (Montreuil et al., 1986). The identification and dosage of the monosaccharides requires hydrolysis by methanolysis of the polymer, in order to only obtain monomers. The glycoside residues are then trimethylsilylated in order to make them volatile. They are thus identified and assayed by gas chromatography in the form of o-trimethylsilylated methylglycosides.

The following reagents are used:
A 3N methanol/HCl solution (Supelco);
Silver carbonate;
Myo-inositol;
Pyridine;
Sylon BFT (BSTFA+TMCS 99:1) reagent (Supelco); and
Dichloromethane.

The operating procedure is the following: 400 µg of the algal extract according to the invention prepared as mentioned above and 50 µg of myo-inositol are placed in a dry bath in the presence of 500 µl of a 3 N methanol/hydrochloric acid mixture (Supelco) for 4 hours at 100° C. After cooling down to room temperature, the methanolysate is neutralized with silver carbonate. The samples are centrifuged for 15 minutes at 3,000 rpm and the supernatant is evaporated under a nitrogen jet. The compounds are then dissolved in 80 µl of pyridine and incubated for 25 minutes at 80° C. with 80 µl of sylon (BSTFA: TMCS, 99:1, Supelco). After gentle evaporation of the excess reagents under a nitrogen jet, the trimethylsilylated methylglycosides are taken up in 500 µl of dichloromethane and then injected into gas chromatography (injection into a column, FID detector: flame ionization). The carrier gas is nitrogen. The column, of the HP-5MS type (30 m, inner diameter 0.25 mm), is apolar. The programme for the rise in temperature is the following: 120° C. maintained for 1 minute, and then a gradient of 1.5° C./min up to 180° C., followed by a gradient of 2° C./min up to 200° C.

Each monosaccharide is identified by comparing its relative retention times relatively to the internal standard, with those of pure monosaccharides treated under the same conditions. A response coefficient is calculated for each monosaccharide relatively to the internal standard in order to define the proportion of each monosaccharide within the polysaccharides of the algal extract according to the invention.

The obtained results are shown in Table 1 below and in FIG. 3.

TABLE 1

Composition of the algal extract according to the invention obtained after analysis of trimethylsilylated derivatives by gas chromatography, expressed by weight based on the total weight of the algal extract; with Ara: Arabinose; Gal: Galactose; Glc: Glucose; Xyl: Xylose; Man: Mannose; Rha: Rhamnose, GlcA: Glucuronic Acid.

| Sample | % by weight of the ultrafiltrate | Ultrafiltration yield | % by weight of the raw extract |
|---|---|---|---|
| Ara | 0.6 | 20.50% | 0.123 |
| Gal | 1.3 | 20.50% | 0.267 |
| Glc | 0.1 | 20.50% | 0.021 |
| Xyl | 2.45 | 20.50% | 0.502 |
| Man | 0.45 | 20.50% | 0.092 |
| Rha | 39.6 | 20.50% | 8.118 |
| GlcA | 12.9 | 20.50% | 2.645 |

Example 4: Evaluation of the Effects of the Algal Extract (AE) Through a Functional Battery of Tests and of Additional Tests (Open Field, Elevated-Plus Maze, Test for Avoiding Aversive Stimulus)

The effects of an algal extract according to the invention (AE) administered orally at doses of 20, 40 and 80 mg/kg for 14 days were evaluated in adult male Wistar rats.

The effects of AE were evaluated on groups of 6 rats as compared with a control batch treated with the carrier (spring water) through a functional battery of tests (FOB). Additional tests, open field, elevated-plus maze and the test for avoiding an aversive light stimulus, were conducted for completing the evaluation of the effects of AE.

The rats used were treated according to the ethical rules dictated by ASAB and the Canadian Council for Animal Protection.

Equipment and Methods

Animals

Twenty four (24) male Wistar Crl:WI (Han) rats (Charles River Laboratories, 69-St-Germain sur l'Arbresle, France) of 60 days of age were used. Upon receiving them, the rats were marked and distributed in groups of 2 in polycarbonate cages of the F type (48×27×20 cm, U.A.R., 91-Epinay-Sur-Orge, France). The animals were confined in an air-conditioned animal housing facility, at a temperature of 22±2° C. and with 50±20% hygrometry. The rats had standard 2016 feed (Mucedola for Harlan, Milan, Italy) and drink ad libitum and were subject to a reverse light-darkness cycle of 12 hours (light from 8 p.m. to 8 a.m.).

After getting used to the laboratory conditions for one week, the rats are weighed and randomly distributed into 4 treatment groups (n=6).

In order to avoid possible interferences between the various products, the rats of a same cage all received the same treatment. The rats of the different groups were all handled in the same way and under the same conditions. The FOB Test The following equipment was used in this test:

a transparent observation cage;
a suspension device;
a gripping device;
an open field for locomotor and exploratory activity;
an auditive stimulation apparatus emitting a standard sound stimulus;
a stylus for various tactile stimulations;
a digital thermometer.

The FOB test was conducted as a blind test before administering the product (T0) and after a period of 14 days of treatment (T14) via an oral route at doses of 20, 40 and 80 mg/kg.

The test included three observation phases:

a direct observation phase during which the animal is not disturbed;
an active observation phase during which the animal was handled;
a phase dedicated to evaluating the behavioural reactions of the animals following reactivity tests.

The recorded variables were the following:

Behavioural effects: spontaneous locomotor activity, locomotor behaviour disorders, flight reaction to being touched, irritability, caused aggressive and freezing behaviours, drowsiness, micturition and defecation, sensorimotor responses (visual placement, pinching the paw, pinching the tail and reaction to a sound stimulus).

Neurological effects: pupil response, palpebral reflex, pelvic elevation, position of the tail, muscular tonicity of the limbs and of the abdomen, rollover test, gripping test, trembling and piloerection.

Physiological effects: salivation, lacrimation, diarrhoea, rectal temperature, cardiac-respiratory rhythm.

Mortality.

The following tests were conducted after two weeks of administration of the products:

Elevated Plus Maze Test (LCS)

The experimental device, with the shape of a cross, is elevated to 80 cm above the ground. It comprises four arms with a length of 50 cm and a width of 15 cm. Two opposite arms are closed by vertical walls with a height of 40 cm, the two other arms being open to empty space, and, consequently represent anxiogenic locations. On day 18, one hour after administration of the treatment, the animal was placed at the centre of the cross of the device and was able to freely access the whole of the four arms. The behaviour of the animal was recorded by means of the ANYMAZE system for 5 minutes. The variables studied in this test were the number of entries into the open arms, as well as the time spent in these open arms. A small number of entries and a short time spent in the open arms are considered as indicating anxiety (Lister, 1987).

Aversive Light Stimulus Avoidance Response (ALSAR) Test

This model uses aversion of the rat for a strongly illuminated environment. The rat learns to master its aversive light environment within the scope of conditioning which operates by pressing on an active lever in order to obtain darkness periods of 30 seconds as a positive reinforcement.

The experimental device consists in a strongly illuminated isolated cage (50×40×37 cm), and including two levers: one active one, allowing when it is actuated, 30 seconds of darkness to be obtained followed by return of the light, while the other lever is inactive (does not cause any positive reinforcement). The pressing actions on the active lever, during the darkness period do not provide additional darkness periods. The rat is placed in the cage for 20 minutes and the number of pressing actions on each lever is counted during the experimentation.

The test battery, consisting of 4 conditioning devices is entirely automated and controlled via a computer. Thus, no experimenter is present in the room during the test.

After 18 days of administration of the products to be tested, the rats were tested on a cognitive level for acquiring training within the scope of conditioning operating in the ALSAR model.

The recorded variables were the total number of pressing actions on the active (LA) and inactive (LI) levers and the numbers of pressing actions on each of both levers during the light phase.

The numbers of active and inactive pressing actions allowed evaluation of the level of manipulatory activity during the test session. Acquiring training (discrimination between both levers) was evaluated by comparing the number of pressure actions on each of the two levers during the light phase (LA vs. LI).

Product

The product is an AE (algal extract) as a powder representing a freeze-dried and crushed concentrated fraction of a water-soluble algal extract prepared according to Example no. 1. The AE is dissolved in spring water and administered orally 60 minutes before the FOB tests and the additional behavioural tests by means of an intragastric feeding probe.

Statistical Analysis

The Kruskal-Wallis test was applied, followed in the cases of heterogeneity, by comparisons by means of the Mann-Whitney U test for comparing the treated groups with the control group.

Wilcoxon's test was used for two-by-two comparisons of the repeated FOB measurements, between T0 and T14 in each of the groups and for discriminating between both ALSAR levers in an illuminated environment.

The statistical and graphical processing operations were carried out by means of the software package StatvieW 5 (SAS Institute, Inc., USA).

Results

FOB Test

Comparisons of the Groups Treated with the Carrier Group in the FOBs at T0 and T14

In the FOB at T0, before administering the treatment, the results of all the studied rat groups are homogeneous (Table 2, Table 3).

In the FOB tests at T14 (after 14 days of administration of the treatments), the Kruskal-Wallis test showed homogeneity of the results within many variables from among the different treatment groups (Table 2).

On the other hand, on certain studied variables, the AE at certain doses showed significant effects as compared with the carrier (Table 3).

The main variables modified by daily administration of AE for two weeks are:

- The behaviour of the rats and their spontaneous locomotor activity in a housing cage: the rats treated with 3 doses are more active and more alert,
- The behaviour of the rats in the observation cage: there also, the rats are more active and more alert with 2 stronger doses,
- Interest for a shown object: at the 3 doses, AE seems to have a stimulating effect on the curiosity of the rats and their interest for novelty (increase in the exploratory activity, hedonism, antidepressant effect),
- The flight reactions of the rats upon approaching a finger or upon touching them are significantly reduced by AE at the 3 doses, which comes under an anti-stress/anxiolytic effect of AE,
- The reactions to pinching of the tail and to pinching of the paw are also significantly reduced at the 3 doses. These lowered reactions come under an anti-stress/anxiolytic effect of AE and/or an antalgic effect,
- The cardiac and respiratory frequencies of the rats seem to be lower than in rats treated with AE at the 3 doses, these come under an anti-stress/anxiolytic effect of AE,
- Agitation, nervosity and irritability of the rats were significantly lowered under administration of AE at the 2 strongest doses, coming under a calming, anti-stress and/or anti-aggressivity effect.

TABLE 2

State of the variables before (T0) and after (T14) administration of AE for 14 days at the doses of 20, 40 and 80 mg/kg, p.o.

| | FOB session | | | | | | | |
|---|---|---|---|---|---|---|---|---|
| | T0 | | | | T14 | | | |
| | | | | Groups | | | | |
| Items | Carrier | AE 20 | AE 40 | AE 80 | Carrier | AE 20 | AE 40 | AE 80 |
| Displacement latency in the arena | $H(ddl3) = 5.14; P = 0.16$ | | | | $H(ddl3) = 4.10; P = 0.25$ | | | |
| Locomotor activity (spaces crossed) | $H(ddl3) = 3.06; P = 0.38$ | | | | $H(ddl3) = 2.43; P = 0.49$ | | | |
| Locomotor activity (straightening up) | $H(ddl3) = 4.91; P = 0.18$ | | | | $H(ddl3) = 2.96; P = 0.40$ | | | |
| Awaken or drowsy condition | $H(ddl3) = 3.00; P = 0.39$ | | | | $H(ddl3) = 0.00; P = 1.00$ | | | |
| Spaces crossed on an open branch | $H(ddl3) = 3.00; P = 0.39$ | | | | $H(ddl3) = 3.94; P = 0.27$ | | | |
| Rollover reaction | $H(ddl3) = 0.00; P = 1.00$ | | | | $H(ddl3) = 0.00; P = 1.00$ | | | |
| Gripping reaction | $H(ddl3) = 1.11; P = 0.77$ | | | | $H(ddl3) = 2.09; P = 0.55$ | | | |
| Suspension test | $H(ddl3) = 3.15; P = 0.37$ | | | | $H(ddl3) = 1.89; P = 0.59$ | | | |
| Jump reaction to a sound stimulus | $H(ddl3) = 4.26; P = 0.23$ | | | | $H(ddl3) = 2.13; P = 0.55$ | | | |
| Caused aggressivity | $H(ddl3) = 0.00; P = 1.00$ | | | | $H(ddl3) = 0.00; P = 1.00$ | | | |
| General muscular tonicity | $H(ddl3) = 3.34; P = 0.34$ | | | | $H(ddl3) = 6.39; P = 0.10$ | | | |
| Limb muscular tonicity | $H(ddl3) = 4.60; P = 0.20$ | | | | $H(ddl3) = 3.29; P = 0.35$ | | | |
| Visual placement reaction on the rod | $H(ddl3) = 5.63; P = 0.13$ | | | | $H(ddl3) = 1.97; P = 0.58$ | | | |
| Shrieks | $H(ddl3) = 2.30; P = 0.51$ | | | | $H(ddl3) = 4.31; P = 0.23$ | | | |
| Defecation | $H(ddl3) = 5.43; P = 0.14$ | | | | $H(ddl3) = 3.22; P = 0.36$ | | | |
| Micturition | $H(ddl3) = 6.27; P = 0.10$ | | | | $H(ddl3) = 2.30; P = 0.51$ | | | |
| Convulsions | $H(ddl3) = 0.00; P = 1.00$ | | | | $H(ddl3) = 0.00; P = 1.00$ | | | |
| Trembling | $H(ddl3) = 0.00; P = 1.00$ | | | | $H(ddl3) = 0.00; P = 1.00$ | | | |
| Diarrhoea | $H(ddl3) = 0.00; P = 1.00$ | | | | $H(ddl3) = 0.00; P = 1.00$ | | | |
| Exophthalmos | $H(ddl3) = 0.00; P = 1.00$ | | | | $H(ddl3) = 0.00; P = 1.00$ | | | |
| Piloerection | $H(ddl3) = 0.00; P = 1.00$ | | | | $H(ddl3) = 0.00; P = 1.00$ | | | |
| Salivation | $H(ddl3) = 0.00; P = 1.00$ | | | | $H(ddl3) = 0.00; P = 1.00$ | | | |
| Lacrimation | $H(ddl3) = 0.00; P = 1.00$ | | | | $H(ddl3) = 0.00; P = 1.00$ | | | |
| Palpebral reflex | $H(ddl3) = 0.00; P = 1.00$ | | | | $H(ddl3) = 0.00; P = 1.00$ | | | |
| Strange behaviours | $H(ddl3) = 0.00; P = 1.00$ | | | | $H(ddl3) = 0.00; P = 1.00$ | | | |
| Bending the trunk | $H(ddl3) = 0.00; P = 1.00$ | | | | $H(ddl3) = 0.00; P = 1.00$ | | | |
| Pelvic elevation | $H(ddl3) = 0.00; P = 1.00$ | | | | $H(ddl3) = 0.00; P = 1.00$ | | | |
| Elevation of the tail | $H(ddl3) = 0.00; P = 1.00$ | | | | $H(ddl3) = 0.00; P = 1.00$ | | | |
| Rectal temperature | $H(ddl3) = 0.17; P = 0.98$ | | | | $H(ddl3) = 3.67; P = 0.30$ | | | |
| Mortality at 24 h | $H(ddl3) = 0.00; P = 1.00$ | | | | $H(ddl3) = 0.00; P = 1.00$ | | | |

TABLE 3

State of the variables before (T0) and after (T14) administration of AE for 14 days at the doses of 20, 40 and 80 mg/kg, p.o.

| | FOB session | | | | | | | |
|---|---|---|---|---|---|---|---|---|
| | T0 | | | | T14 | | | |
| | | | | Groups | | | | |
| Items | Carrier | AE 20 | AE 40 | AE 80 | Carrier | AE 20 | AE 40 | AE 80 |
| Behaviour of the rat in the housing cage | $H(ddl3) = 5.15; P = 0.16$ | | | | $H(ddl3) = 19.97; P = 0.0002$ (D1** - D2** - D3**) | | | |
| Behaviour of the rat in the observation cage | $H(ddl3) = 4.02; P = 0.26$ | | | | $H(ddl3) = 7.19; P = 0.066$ (D2# - D3*) | | | |
| Spontaneous locomotor activity in the housing cage | $H(ddl3) = 4.33; P = 0.23$ | | | | $H(ddl3) = 15.20; P = 0.008$ (D1** - D2** - D3**) | | | |
| Interest for a shown object (curiosity) | $H(ddl3) = 4.86; P = 0.18$ | | | | $H(ddl3) = 6.86; P = 0.08$ (D1* - D2# - D3*) | | | |
| Flight reaction upon approaching a finger | $H(ddl3) = 2.39; P = 0.50$ | | | | $H(ddl3) = 6.65; P = 0.08$ (D1#- D2#- D3*) | | | |
| Reaction to pinching the tail | $H(ddl3) = 5.50; P = 0.14$ | | | | $H(ddl3) = 15.07; P = 0.002$ (D1** - D2** - D3**) | | | |
| Reaction to pinching a hind paw | $H(ddl3) = 4.13; P = 0.25$ | | | | $H(ddl3) = 9.63; P = 0.02$ (D1** - D2# - D3#) | | | |
| Flight reaction to being touched | $H(ddl3) = 2.12; P = 0.55$ | | | | $H(ddl3) = 8.01; P = 0.045$ (D1* - D2# - D3#) | | | |
| Cardiac and respiratory frequency | $H(ddl3) = 4.60; P = 0.20$ | | | | $H(ddl3) = 10.78; P = 0.01$ (D1# - D2** - D3**) | | | |
| Caused freezing | $H(ddl3) = 3.00; P = 0.39$ | | | | $H(ddl3) = 6.27; P = 0.09$ | | | |

TABLE 3-continued

State of the variables before (T0) and after (T14) administration
of AE for 14 days at the doses of 20, 40 and 80 mg/kg, p.o.

| | FOB session | | | | | | | |
|---|---|---|---|---|---|---|---|---|
| | T0 | | | | T14 | | | |
| | | | | Groups | | | | |
| Items | Carrier | AE 20 | AE 40 | AE 80 | Carrier | AE 20 | AE 40 | AE 80 |
| Muscular tonicity of the abdomen | H(ddl3) = 3.83; P = 0.28 | | | | H(ddl3) = 8.52; P = 0.04 (D2# - D3*) | | | |
| Agitation-nervosity-Irritability | H(ddl3) = 1.04; P = 0.79 | | | | H(ddl3) = 6.77; P = 0.08 (D2# - D3*) | | | |

P < 0.10;
*P < 0.05;
**P < 0.01 (Mann-Whitney Test: vs. Carrier)

Comparisons of the Different Repeated Variables Between the FOBs at T0 and T14

Daily administration of AE at certain doses for 14 days seems to have an effect on certain studied main variables (Table 4):

The behaviour of the rats and their spontaneous locomotor activity in the observation cage significantly increased under AE at the 3 doses (stimulating effect or anti-stress effect), The displacement latency of the control rats in the observation arena increases and their locomotor activity (crossed spaces) decreases, while in rats treated with AE, these variables remain stable between the T0 and T14 FOBs (anti-stress and antidepressant effects), The interest for a shown object: at the dose of 20 mg/kg, p.o. (per os), AE stimulates the interest of the rats for a stimulus object which is presented to them (motivation for exploring novelty, hedonism: anti-stress and antidepressant effects), The number of crossed spaces on an open branch: comparatively with the carrier, AE does not decrease the number of crossed spaces on an open branch (anti-stress effect), The flight reactions upon approaching the finger: AE at the 3 doses decreases the flight reaction upon approaching the finger of the experimenter (anti-stress effect), The reaction to pinching the tail increases in the control rat, while under 20 mg/kg of AE it decreases (anti-stress effect and/or antalgic effect), The reaction to pinching a hind paw decreases under AE, at the 3 doses (anti-stress effect and/or antalgic effect), The jump reaction to a sound stimulus significantly decreases at the AE doses of 40 and 80 mg/kg (calming and anti-stress effects), The cardiac and respiratory frequencies decrease under AE at the doses of 20 and 40 mg/kg (calming and anti-stress effects), Agitation, nervosity and irritability: at the strong dose of 80 mg/kg, AE shows a positive effect on agitation, nervosity and irritability of the rats (calming, anti-stress and/or anti-aggressivity effects).

TABLE 4

Effects of AE on the time-dependent change of the variables between the FOBs at T0 and T14 in each treatment group

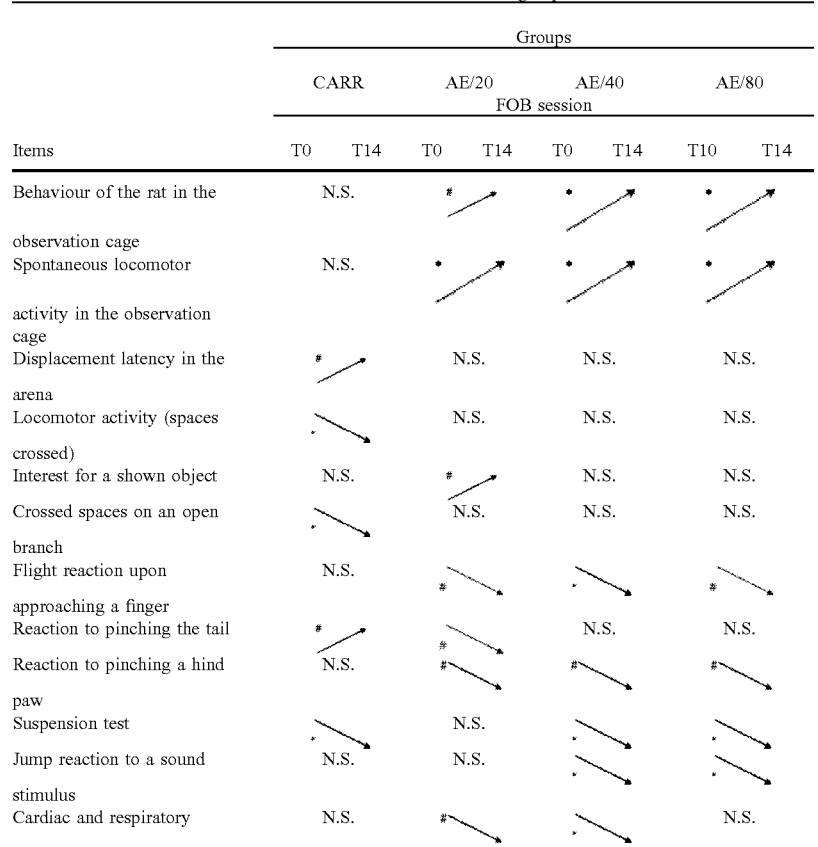

TABLE 4-continued

Effects of AE on the time-dependent change of the variables between the FOBs at T0 and T14 in each treatment group

| | Groups | | | | | | | |
|---|---|---|---|---|---|---|---|---|
| | CARR | | AE/20 | | AE/40 | | AE/80 | |
| | FOB session | | | | | | | |
| Items | T0 | T14 | T0 | T14 | T0 | T14 | T10 | T14 |
| frequency | | | | | | | | |
| Muscular tonicity of the abdomen | # ↘ | | N.S. | | N.S. | | N.S. | |
| Agitation-nervosity-irritability | N.S. | | N.S. | | N.S. | | # ↘ | |

N.S.: Not significant between T0 and T14

↘ Decreases between T0 and T14

↗ Increases between T0 and T14

*P < 0.05;
P < 0.10 (trend)

Elevated Plus Maze Test (LCS)

In the elevated-plus maze test, after 18 days of daily treatment, AE at the doses of 20, 40 and 80 mg/kg, p.o., significantly increases the number of entries (Table 5, FIG. 4) as well as the spent time (Table 6, FIG. 5) of the rats treated in the open arms, demonstrating anti-stress activity of AE.

TABLE 5

Effects of AE on the number of entries into the open arms in the elevated plus maze test

| Products | Carrier (n = 6) | AE 20 mg/kg (n = 6) | AE 40 mg/kg (n = 6) | AE 80 mg/kg (n = 6) | Kruskal-Wallis test |
|---|---|---|---|---|---|
| Number of entries into the open branches Mean (QI-QS) | 1.5 (1.0-4.0) | 4.0 (4.0-5.0) | 5.0 (3.0-5.0) | 4.5 (2.0-5.0) | H(ddl3) = 6.08 P = 0.108 |

TABLE 6

Effects of AE on the time spent in the open arms in the elevated-plus maze test

| Products | Carrier (n = 6) | AE 20 mg/kg (n = 6) | AE 40 mg/kg (n = 6) | AE 80 mg/kg (n = 6) | Kruskal-Wallis Test |
|---|---|---|---|---|---|
| Time spent in the open branches Mean (QI-QS) | 10.0 (7.0-29.0) | 37.5 (32.0-50.0) | 50.5 (38.0-66.0) | 37.0 (17.0-45.0) | H(ddl3) = 7.76 P = 0.051 |

Aversive Light Stimulus Avoidance Response Test (AL-SAR)

After 18 days of daily administration of AE, the Kruskal-Wallis test showed that the number of cumulated pressing actions on both levers (active lever+inactive lever) of the rats of the different treatment groups are homogeneous at 5 minutes, 10 minutes, 15 minutes and at 20 minutes (FIG. 6).

In the test for avoiding an aversive light stimulus, at the end of the first 5 minutes of the test, after 18 days of administration of AE, the rats treated with the dose of 20 mg/kg, p.o., tend to discriminate the active lever from the inactive lever (FIG. 7).

At the end of the period of 10 minutes of the test, the rats treated with AE at the dose of 40 mg/kg, p.o., significantly discriminate the active lever from the inactive lever and those treated with doses of 20 and 80 mg/kg, p.o., tend to operate a discrimination between both levers. This is not the case of the control rats which do not show any trend towards discrimination (FIG. 8).

At the end of the period of 15 minutes of test, the rats treated with AE at the doses of 20 and 40 mg/kg, p.o., significantly discriminate the active lever from the inactive lever. The rats treated at the dose of 80 mg/kg, p.o., no longer discriminate both levers. The control rats still do not show any discrimination at this stage of the training test (FIG. 9).

At the end of the period of 20 minutes of test, the rats treated with AE at the doses of 20 and 40 mg/kg, p.o., still discriminate significantly the active lever from the inactive lever. The rats treated with the dose of 80 mg/kg, p.o., no longer show any discrimination and the control rats begin to exhibit a beginning of discrimination (FIG. 10).

These results show the efficiency of AE on acquiring training, and notably at the doses of 20 and 40 mg/kg, p.o.

Physiological and Innocuity Data

Administration of AE, regardless of the dose, did not show any influence on the weight of the rats daily treated with the doses of 20, 40 or 80 mg/kg, p.o., or on their food intake. No toxicity was detected in animals treated with AE at the doses of 20, 40 and 80 mg/kg/d, p.o., for 21 days.

Conclusion

The administration of an algal extract according to the present invention thus shows the neurological effects of the product, notably the anti-stress/anxiolytic, anti-depressant, antalgic activities as well as an early acquisition activity of training and of facilitating memorization.

Example 5: Evaluation of the Effects of the Algal Extract (AE) Through the Behavioural Despair Test The anti-depressant effects of an algal extract according to the invention (AE), administered orally as a preventive treatment with 3 doses (10, 20 and 40 mg/kg/d) were evaluated in adult male Wistar rats in the behavioural despair test (BDT).

The extract was daily administered as a semi-chronic treatment for 14 days. The effects of the extract were evaluated in the BDT on groups of 12 rats as compared with a control batch treated with the carrier (spring water) and a reference batch treated with Imipramine at the dose of 10 mg/kg/d.

The rats used were treated according to the ethical rules dictated by ASAB and the Canadian Council for Animal Protection.

Equipment and Methods
Animals

Sixty male Wistar rats (Charles River Laboratories, France) weighing from 200-225 g were used. Upon receiving them, the rats were marked and distributed in groups of 4 in polycarbonate cages of the F type (48×27×20 cm, U.A.R., 91-Epinay-Sur-Orge, France). The animals were housed in an air-conditioned animal housing facility, at a temperature of 22±2° C. and a relative humidity of 50±20%. The rats had standard feed 2016 (Harlan, Gannat, France) and drink ad libitum. They were subject to a reverse light-darkness cycle of 12 hours.

After getting used to the conditions of the laboratory for one week, the rats were weighed and randomized according to their weight in 5 treatment groups (n=12/group).

Treatment Groups:
Control group: treatment with spring water (Carrier),
Imipramine group: treatment with Imipramine at the dose of 10 mg/kg/d (Imi),
AE group 10: treatment with AE at the dose of 10 mg/kg/d (AE 10),
AE group 20: treatment with AE at the dose of 20 mg/kg/d (AE 20),
AE group 40: treatment with AE at the dose of 40 mg/kg/d (AE 40).

In order to avoid possible interferences between the different treatments, the rats of a same cage all receive the same dose of AE. The rats of the different groups are all handled in the same way and under the same conditions.

Behavioural Despair Test (BDT)

The experimental devices consisted in Plexiglas cylinders with a height of 50 cm and a diameter of 20 cm filled with water at 25° C. up to a height of 30 cm.

After 13 days of daily treatment with the products to be tested, the rats were placed at D14 in the devices for a period of 15 minutes in order to evaluate the immobility time of each animal. Immediately after this first test, the rats received their 14th treatment.

At D15, the rats received two treatments: the first, 5 hours before the test and the second 1 hour before the test. This procedure is usually used in the literature for testing the efficiency of a product against depression. The test was conducted under the same conditions as the day before for a period of 5 minutes.

The recorded immobility duration during the first 5 minutes of both tests (at D14 and D15) reflects the capacity of the animal of resigning itself when it is confronted with a situation from which it cannot escape. This resignation behaviour is assimilated with depression.

Product

The product is an AE (algal extract) as a powder representing a freeze-dried and crushed concentrated fraction of a water-soluble algal extract prepared according to Example no. 1. The extract to be tested was dissolved in spring water and was administered to the rats orally at one of the 3 tested doses for 15 successive days with an administration volume of 5 ml/kg. The animals were weighed every two or three days in order to adapt their specific treatments to their weight. Their food and water intakes were noted every two or three days during the whole duration of the study.

The animals of the Reference group receive daily 10 mg/kg/d of Imipramine hydrochloride (Sigma Aldrich) dissolved in spring water with an administration volume of 5 ml/kg.

The animals of the Carrier group daily received spring water with an administration volume of 5 ml/kg.

Statistical Analysis

ANOVA in parametric mode was applied, followed, in the case of heterogeneity, by comparisons by means of the non-paired t-test for comparing the treated groups with the Carrier group and the Reference group.

Paired ANOVA was used, followed, in the case of heterogeneity, by comparisons with the paired t-test for two by two comparisons of repeated measurements of BDT in each of the groups.

For the food and water intakes, non-parametric mode analysis was applied: a Kruskal-Wallis test if necessary followed by a Mann Whitney U test for comparing the groups two by two.

The statistical and graphic processing operations were achieved by means of the software package Statview5 (SAS Institute, Inc., USA).

Results

Behavioural Despair Test: Pre-Test at D14

At D14, in the pre-test of the behavioural despair, ANOVA did not show any heterogeneity for the immobility times of the animals of the different treatment groups (Table 7; FIG. 11). This pre-test gives the possibility of obtaining induction of resignation in the animals of the different treatment groups.

TABLE 7

Effects of AE on the immobility time(s) in the behavioural despair pre-test at D14 (s, Average ± SME)

| | Products | | | | | |
|---|---|---|---|---|---|---|
| | Carrier (n = 12) | Imipramine 10 mg/kg (n = 12) | AE 10 mg/kg (n = 12) | AE 20 mg/kg (n = 12) | AE 40 mg/kg (n = 12) | ANOVA$_{(ddl\ =\ 4)}$ |
| Immobility duration (s) | 18.7 ± 3.6 | 16.3 ± 4.6 | 12.5 ± 3.8 | 9.8 ± 3.2 | 9.3 ± 1.8 | F = 1.33 P = NS |

NS: non-significant.

Behavioural Despair Test at D15

At D15, in the behavioural despair test, ANOVA showed heterogeneity for the immobility time of the animals of the different treatment groups (Table 8).

The non-paired t-test showed that the immobility times of the animals treated with Imipramine, AE 20 and AE 40 were significantly shorter than that of the animals with the Carrier (t=3.69, P=0.0013; t=2.20, P=0.039 and t=3.29, P=0.003, respectively).

The non-paired t-test showed that the immobility time of the animals treated with AE 20 tended to be significantly longer than that of the animals treated with Imipramine (t=1.72, P=0.099) (Table 8; FIG. 12).

the animals of the other groups, no significant difference was observed between the rats treated with the Carrier, Imipramine and AE administered at the three tested doses.

At D15:

the anti-depressant effect of AE administered at the doses of 20 and 40 mg/kg was ascertained since the immobility durations of the animals treated at these doses were significantly shorter than those of the animals treated with the Carrier. AE administered at the dose of 40 mg/kg gave the possibility of obtaining an immobility duration similar to that of the animals treated with Imipramine at 10 mg/kg. A dose-dependent effect was observed in animals treated with AE at the doses of 10, 20 and 40 mg/kg.

TABLE 8

Effects of AE on the immobility duration(s) in the behavioural despair test at D15 (s, Average ± ESM)

| | | Products | | | |
|---|---|---|---|---|---|
| | Carrier (n = 12) | Imipramine 10 mg/kg (n = 12) | AE 10 mg/kg (n = 12) | AE 20 mg/kg (n = 12) | AE 40 mg/kg (n = 12) | ANOVA$_{(ddl-4)}$ |
| Immobility duration (s) | 14.4 ± 2.7 | 3.8 ± 1.0 | 12.0 ± 5.0 | 7.3 ± 1.8 | 4.9 + 1.0 | F = 2.76 P = 0.036 |
| Non-paired t-test (vs. Carrier) | | t = 3.69 P = 0.0013 | t = 0.42 NS | t = 2.20 P = 0.039 | t = 3.29 P = 0.003 | |
| Non-paired t-test (vs. Imipramine) | | | t = 1.60 P = NS | t = 1.72 T (P = 0.099) | t = 0.75 NS | |
| Non-paired t-test (vs. AE 10) | | | | t = 0.98 NS | t = 1.38 NS | |
| Non-paired t-test (vs. AE 20) | | | | | t = 1.17 NS | |

NS: not significant.

Comparison of the Results of the Tests at D14 and D15

The paired t-test showed that the immobility times of the rats treated with Imipramine and AE 40 significantly decrease between D14 and D15 (t=2.90, P=0.015 and t=2.42, P=0.034, respectively) (Table 9).

TABLE 9

Comparison of the results of the tests at D14 and D15 (s, Average ± SME)

| Products | Carrier (n = 12) | Imipramine 10 mg/kg (n = 12) | AE 10 mg/kg (n = 12) | AE 20 mg/kg (n = 12) | AE 40 mg/kg (n = 12) |
|---|---|---|---|---|---|
| Immobility duration (s) at D14 | 18.7 ± 3.6 | 16.3 ± 4.6 | 12.5 ± 3.8 | 9.8 ± 3.2 | 9.3 ± 1.8 |
| Immobility duration (s) at D15 | 14.4 ± 2.7 | 3.8 ± 1.0 | 12.0 ± 5.0 | 7.3 ± 1.8 | 4.9 ± 1.0 |
| Paired t-test | | | | | |
| t= | 1.41 | 2.90 | 0.11 | 1.10 | 2.42 |
| P= | NS | 0.015 | NS | NS | 0.034 |

NS: not significant.

Weight Evolution, Food and Water Intakes

No effect of AE administered at the three doses was shown as regards the weight evolution and the food and water intakes of the animals.

Behavioural Despair Test

At D14:

during the test for setting resignation in the animals, although the immobility duration of the animals treated with AE at the doses of 20 and 40 mg/kg is shorter than those of Comparison of the Immobility Durations at D14 and D15:

only the animals treated with Imipramine at the dose of 10 mg/kg and with AE at the dose of 40 mg/kg have significantly reduced their immobility duration between D14 and D15.

Behaviour of the Animals and Innocuity of the Algal Extract

No abnormal behaviour of the whole of the animals was observed during the experimentation for AE administered at the doses of 10, 20 and 40 mg/kg. No toxicity was detected in animals treated with AE at the doses of 10, 20 and 40 mg/kg/d for 14 days.

Conclusion

The administration of an algal extract according to the present invention thus demonstrates an anti-depressant effect of the product.

The invention claimed is:

1. A method for treating depression, the method comprising the administration, to a subject in need thereof, of an effective amount of an algal extract from the order of Ulvales comprising sulphated and non-sulphated polyanionic polysaccharides, the size of which is less than or equal to 50 kDa, wherein the algal extract is prepared by a process comprising the following steps:
   a) washing the algae and freeing the algae of sand;
   b) crushing the washed and freed algae to create a crushed product comprising a solid phase and a liquid phase;
   c) separating the solid phase of the crushed product from the liquid phase of the crushed product;
   d) clarifying the separated liquid phase to form a juice;
   e) filtering the juice with a membrane of less than 50 kDa; and f) concentrating the filtered juice; and
g) drying the concentrated juice.

2. The method according to claim 1, wherein the extract is an extract of green algae of the type Ulva.

3. The method according to claim 1, wherein said polysaccharides comprise mannose and/or arabinose.

4. The method according to claim 3, wherein said polysaccharides comprise at least 0.005% of mannose and/or at least 0.005% of arabinose, by weight based on the weight of the total dry material of the algal extract.

5. The method according to claim 4, wherein said polysaccharides comprise mannose at an amount in a range from 0.01 to 0.20% and arabinose at an amount in the range of 0.01 to 0.5%, by weight based on the weight of the total dry material of the algal extract.

6. The method according to claim 1, wherein said polysaccharides further comprise
galactose, glucose, rhamnose, xylose, and glucuronic acid.

7. The method according to claim 6, wherein:
the galactose is at an amount in the range of 0.05 to 0.5%;
the glucose is at an amount in the range of 0.005 to 0.05%;
the rhamnose is at an amount in the range of 2 to 15%;
the xylose is at an amount in the range of 0.1 to 1%; and
the glucuronic acid is at an amount in the range of 1 to 7%;
by weight based on the weight of the total dry material of the algal extract.

8. The method according to claim 1, wherein said polysaccharides have a size of less than or equal to 15 kDa.

9. The method according to claim 1, wherein the algal extract comprises:
carbon at an amount in the range of 10 to 50%;
hydrogen at an amount in the range of 1 to 10%;
nitrogen at an amount in the range of 1 to 5%;
oxygen at an amount in the range of 20 to 50%; and
sulphur at an amount in the range of 1 to 15%;
in weight percentage of the total dry material of the algal extract.

10. The method according to claim 1, wherein the algal extract comprises:
carbon at an amount in the range of 15 to 30%;
hydrogen at an amount in the range of 3 to 6%;
nitrogen at an amount in the range of 1 to 3%;
oxygen at an amount in the range of 25 to 40%; and
sulphur at an amount in the range of 2.5 to 10%;
in weight percentage of the total dry material of the algal extract.

11. The method according to claim 1, wherein membrane is a 15 kDa membrane.

12. The method according to claim 1, wherein solid phase is separate from the liquid phase by pressing the crushed product.

13. The method according to claim 1, wherein:
the algae is washed in freshwater;
the algae are crushed with a refiner;
the solid phase of the crushed product is separated from the liquid phase of the crushed product by pressing the crushed product with a belt press;
the separated liquid phase is clarified with a clarifier with disc stacks;
the membrane is a 15 kDa ceramic membrane;
the filtered juice is concentrated by evaporation; and/or
the concentrated juice is dried by freeze-drying or atomization.

14. The method according to claim 1, wherein the composition further comprises for at least one pharmaceutically acceptable excipient.

* * * * *